(12) United States Patent
Budri et al.

(10) Patent No.: US 8,481,142 B1
(45) Date of Patent: Jul. 9, 2013

(54) SYSTEM AND METHOD FOR MONITORING CHLORIDE CONTENT AND CONCENTRATION INDUCED BY A METAL ETCH PROCESS

(75) Inventors: Thanas Budri, Portland, ME (US); Thomas Francis, South Portland, ME (US); David Tucker, Falmouth, ME (US); Stephen W. Swan, Windham, ME (US); Sergei Drizlikh, Scarborough, ME (US)

(73) Assignee: National Semiconductor Corporation, Santa Clara, CA (US)

( * ) Notice: Subject to any disclaimer, the term of this patent is extended or adjusted under 35 U.S.C. 154(b) by 706 days.

(21) Appl. No.: 11/215,845

(22) Filed: Aug. 30, 2005

(51) Int. Cl.
*H01L 21/302* (2006.01)

(52) U.S. Cl.
USPC .............................. 428/72; 216/59; 428/710

(58) Field of Classification Search
USPC .......................................................... 438/720
See application file for complete search history.

(56) References Cited

U.S. PATENT DOCUMENTS

| | | | | |
|---|---|---|---|---|
| 5,534,728 | A * | 7/1996 | Kim et al. | 257/692 |
| 5,820,746 | A * | 10/1998 | Kawaguchi et al. | 205/791 |
| 6,461,971 | B1 * | 10/2002 | Ianovitch | 438/710 |
| 6,526,996 | B1 * | 3/2003 | Chang et al. | 134/1.3 |

OTHER PUBLICATIONS

Singh et al (Detection and Characterization of Trace Element Contamination on Silicon Wafer; AIP Conference Proceedings; Jan. 24, 2003; vol. 652, pp. 472-480).*

Mori et al. (Sweeping TXRF: A Nondestructive Technique for the Entire Surface Characterization of Metal Contaminations on Semiconductor Surfaces IEEE Transactions on Semiconductor manufacturing, vol. 18, No. 4, Nov. 2005).*

Sparks et al. (Evaluation of the Contamination mapping Capabilities with TXRF; Analytical Chemistry, 2002, 74, pp. 1104-1110, vol. 45).*

Wolf et al. (Silicon Processing for the VLSI Era; vol. 1; 1986; Lattice Press).*

Sparks (TXRF to Monitor for High Dielectric Material Contamination in a Semiconductor Fab; JCPDS—International Centre for Diffraction Data 2002, advances in X-ray Analysis, vol. 45).*

Mori et al. (Detection of unknown localized contamination on silicon wafer surface by sweeping-total reflection X-ray fluorescence analysis; Spectrochimica Acta Part B: Atomic Spectroscopy; vol. 59; Issue 8, Aug. 31, 2004).*

Kern (Handbook of Semiconductor Wafer Cleaning Technology: Science, Technology, and Applications; 1993; William Andrew Inc.; ISBN 0815513313).*

(Continued)

*Primary Examiner* — Patricia George
(74) *Attorney, Agent, or Firm* — Eugene C. Conser; Wade J. Brady, III; Frederick J. Telecky, Jr.

(57) ABSTRACT

A system and method for monitoring chloride content and concentration induced by a metal etch process is disclosed. A blank metal film is deposited on a semiconductor wafer. A metal etch process is then applied to partially etch the blank metal film on the wafer. The metal etch process exposes the metal film to chlorine. The wafer is then scanned using surface profiling total X-ray reflection fluorescence. A chlorine concentration map is generated that shows quantitative and spatial information about the chlorine on the wafer. Information from the chlorine concentration map is then used to select a value of chlorine concentration for a metal etch process that will not create metal chloride corrosion on a semiconductor wafer.

20 Claims, 8 Drawing Sheets

OTHER PUBLICATIONS

Mori et al. (herein referred to as Mori 2) (Whole surface analysis of semiconductor wafers by accumulating short time mapping data of TXRF spectrometry; Analytical Chemistry, vol. 74, No. 5, Mar. 1, 2002).*

Mori et al. (Sweeping TXRF: A non destructive technique for the entire surface characterization of metal contaminations on semiconductor wafers; 2003).*

A. Daniel (Surface Profiling; TXRF'05 conference presentation, held in Budapest, Sep. 19-23, 2005; published and made available to the public about Aug. 14, 2005).*

Daniel; CEA 2006; http://www-ist.cea.fr/publicea/exl-doc/200600005299_2.pdf.*

Fan; Abstract of a wafer level corrosion . . . ;RPS 1988.*

Fan; A wafer level corrosion . . . ;RPS 1988.*

Borde et al.;Sweeping total reflection X-ray fluorescence optimisation to monitor the metallic contamination into IC manufacturing; ST Microelectronics, online Oct. 29, 2008 provides evidence that the scan of one point with an TXRF system inherently monitors an area of 1 mm2, see figure 3.*

Zhao ( Solid State Technology; Mar. 2003; Using TXRF to Monitor Phosphorus Cross Contamination in Implanters).*

* cited by examiner

TXRF Analysis $^{63}$Cu in TiN Over the AlCu 2KA (Control Wafer)

| | | | | |
|---|---|---|---|---|
| Filename | : TXRF2027.SWM | Points | : | 181 |
| X-Ray | : 30 kV  300 mA | Size | : | 200 mm |
| Date | : 05/03/23  22:59:00 | Time | : | 5 sec |
| Sample ID | : 31ot04  2K  AlCu | Slot | : | 4 |
| Group | : B207 | Beam | : | W-Lb |

SYSTEM AND METHOD FOR MONITORING CHLORIDE CONTENT AND CONCENTRATION INDUCED BY A METAL ETCH PROCESS

TECHNICAL FIELD OF THE INVENTION

The present invention is generally directed to manufacturing technology for semiconductor devices and, in particular, to an efficient system and method for monitoring chloride content and concentration induced by a metal etch process.

BACKGROUND OF THE INVENTION

A common problem encountered during the manufacture of a semiconductor device is the undesirable creation of corrosion of the metal lines of the semiconductor device. A commonly used metal is a combination of aluminum (Al) and copper (Cu) in which the copper is approximately one half of one percent (0.5%) of the combination.

A significant portion of the metal corrosion of the aluminum copper (AlCu) layers in a semiconductor device is caused by chlorine that is present is a plasma etch process that is used to etch the metal layers. The chlorine is supposed to be removed from the metal layers during post metal etch cleaning processes. However, sometimes the cleaning processes do not efficiently strip the chlorine residues. The chlorine residues that are not removed interact chemically with the metal layers to form corrosion in the form of metal chlorides (e.g., aluminum chloride and copper chloride).

Figure 1:
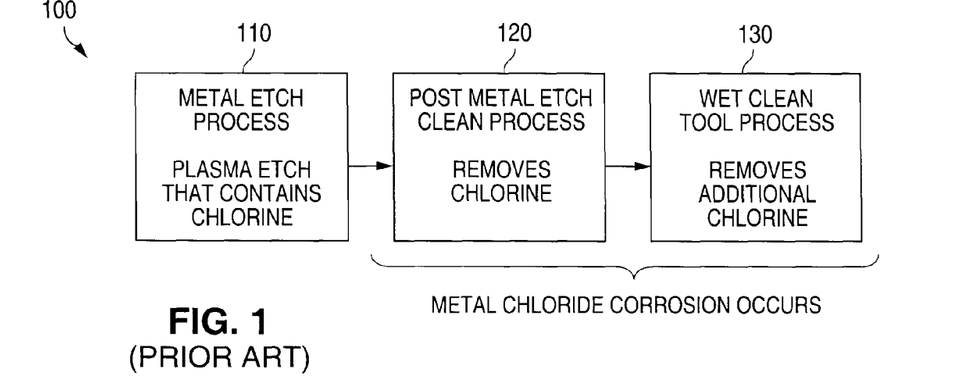
FIG. 1 illustrates an exemplary prior art metal etch process and post metal etch clean processes showing process steps in which metal chloride corrosion occurs.

FIG. 1 illustrates an exemplary prior art process 100 that comprises a metal etch process 110, and a post metal etch clean process 120 and a subsequent wet tool clean process 130. The metal etch process 110 is carried out by a plasma etch process that contains chlorine. For example, the metal etch process 110 may comprises a process that utilizes a plasma to etch the aluminum of an aluminum metal interconnect stack in a semiconductor device. One example of a plasma etch formulation that contains chlorine comprises boron trichloride and nitrogen and chlorine ($BCl_3 + N_2 + Cl_2$).

After the metal etch process 110 has been completed a post metal etch clean process 120 is performed. The post metal etch clean process 120 is designed to remove the chlorine from the metal surfaces. A subsequent wet clean tool process 130 is then applied to provide additional cleaning of the surfaces of a wafer that contains the semiconductor devices. The wet clean tool process 130 removes additional amounts of residual chlorine.

The post metal etch clean process 120 and the wet clean tool process 130 may not remove all of the chlorine that is left on the wafer from the metal etch process 110. The chlorine reacts chemically with water vapor that is present in the atmosphere and combines with the metal surfaces to form metal chlorides. When the chlorine combines with aluminum then aluminum chloride is formed. When the chlorine combines with copper then copper chloride is formed. When the chlorine combines with an aluminum copper mixture then a mixture of aluminum chloride and copper chloride is formed.

Figure 2:
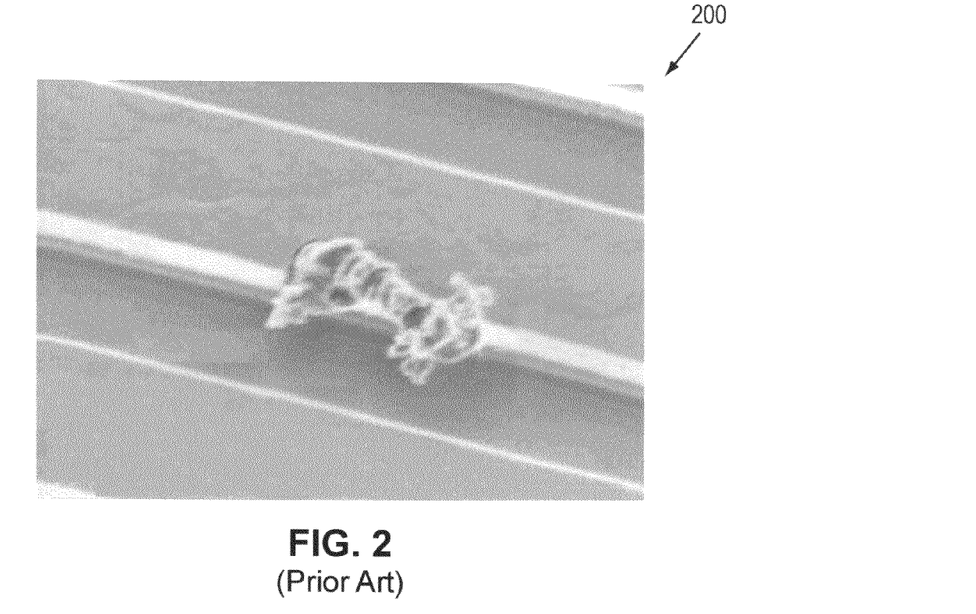
FIG. 2 illustrates a photograph showing an example of a prior art metal chloride corrosion formed on a metal line following a metal etch process.

The interaction of chlorine with the metal material creates several different types of corrosion of the metal portions (e.g., metal interconnect lines) of the semiconductor device. One type of corrosion occurs when aluminum (Al) and copper (Cu) are exposed to Chlorine (Cl) and water ($H_2O$). FIG. 2 illustrates a photograph 200 showing an example of one type of metal chloride corrosion formed on a metal line due to the presence of chlorine. The corrosion process may occur during the post metal etch clean process 120 and later during the wet clean tool process 130.

It would be desirable to have an efficient method for detecting the presence of metal corrosion due to chlorine during the manufacture of semiconductor devices. One prior art approach to detecting the presence of chlorine induced corrosion involves the use method that is called the "wet box test." The wet box test typically used by plasma etch engineers to determine whether or not a semiconductor wafer has metal corrosion on it.

The wet box test comprises exposing a semiconductor wafer that is to be tested to a very humid atmosphere (i.e., an atmosphere having a high level of water vapor in it). The wafer is placed in the very humid atmosphere (or even immersed within a container of water) and left for an extended period of time. The wet box test can take from six (6) hours to twenty four (24) hours. Then the wafer is removed, dried and inspected. If there is no visible corrosion then the wafer has successfully passed the test. The wafer fails the test if corrosion is found.

The results of the wet box test are very qualitative. The wet box test is also rather time consuming. Therefore, it would be advantageous to have a more efficient system and method for determining the presence of chloride content and concentration in a semiconductor wafer that is induced by a metal etch process.

Before undertaking the Detailed Description of the Invention below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Definitions for certain words and phrases are provided throughout this patent document, those of ordinary skill in the art should understand that in many, if not most instances, such definitions apply to prior uses, as well as future uses, of such defined words and phrases.

BRIEF DESCRIPTION OF THE DRAWINGS

For a more complete understanding of the present invention and its advantages, reference is now made to the following description taken in conjunction with the accompanying drawings, in which like reference numerals represent like parts.

DETAILED DESCRIPTION OF THE INVENTION

FIGS. 3 through 10, discussed below, and the various embodiments used to describe the principles of the present invention in this patent document are by way of illustration only and should not be construed in any way to limit the scope of the invention. Those skilled in the art will understand that the principles of the present invention may be implemented in any type of suitably arranged semiconductor wafer.

The method of the present invention is designed to acquire quantitative information concerning the content and concentration of chlorine in a semiconductor wafer. Unlike prior art methods the method of the present invention is able to obtain the desired information very quickly.

Figure 3:
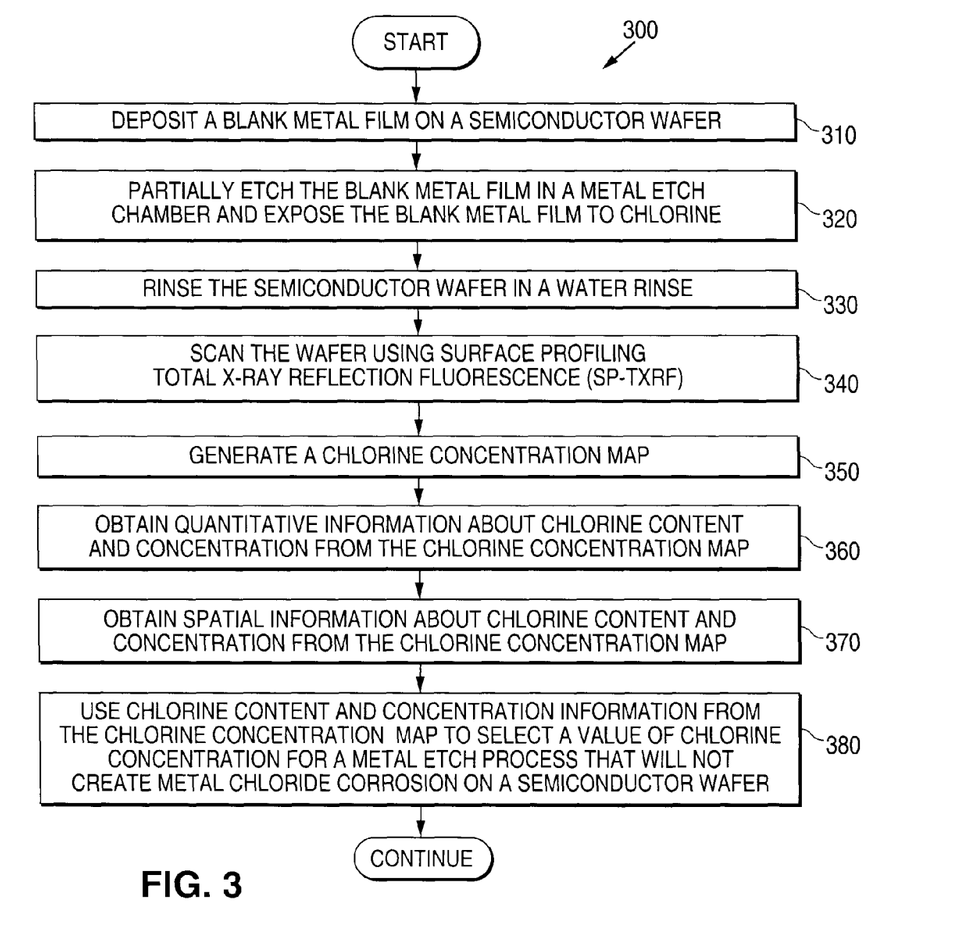
FIG. 3 illustrates a flow chart showing an advantageous embodiment of a method of the invention.

FIG. 3 illustrates a flow chart 300 showing an advantageous embodiment of a method of the present invention. In the first step of the method a blank metal film (e.g., a film of aluminum copper) is deposited on a semiconductor wafer (step 310). Then the blank metal film is partially etched in a metal etch chamber (step 320). The metal etch process exposes the blank metal film to chlorine. Then the semiconductor wafer is rinsed in a water rinse (step 330). This removes most of the chlorine.

Then the surface of the semiconductor wafer is scanned using surface profiling (SP) total X-ray reflection fluorescence (TXRF) (step 340). The results of the scanning step are used to generate a chlorine concentration map of the semiconductor wafer (step 350). Quantitative information (i.e., numerical information) about the chlorine content and concentration on the semiconductor wafer is obtained from the chlorine concentration map (step 360). Spatial information (i.e., location information) about the chlorine content and concentration on the semiconductor wafer is obtained from the chlorine concentration map (step 370).

The chlorine content and concentration information from the chlorine concentration map is then used to select a value of chlorine concentration for a metal etch process that will not create metal chloride corrosion on a semiconductor wafer (step 380).

Unlike prior art methods, the method of the present invention provides useful results immediately after the surface profiling (SP) total X-ray reflection fluorescence (TXRF) test has been completed. The test results provide a quantitative measurement of how much chlorine is on the tested wafer. The precision of the test provides results having a resolution of one atom in $10^{11}$ atoms (of chlorine) per square centimeter.

By testing a number of different wafers with a number of different chlorine concentrations it is possible to identify a threshold value of chlorine concentration (for a particular type of semiconductor wafer). Chlorine concentrations that are above the threshold value cause metal chloride corrosion to occur on the wafer. Chlorine concentrations that are below the threshold value do not cause metal chloride corrosion to occur. The method of the present invention can be applied to find the appropriate threshold value of chlorine concentration in the plasma of the metal etch process to be applied. By keeping the level of chlorine concentration in the plasma of the metal etch process below the threshold level, the metal etch process will not induce metal chloride corrosion in the wafers that are subjected to the metal etch process.

The method of the present invention has been successfully applied to production semiconductor wafers. The method of the present invention is well suited to be used to monitor production line performance for manufacturing semiconductor wafers. The method of the present invention is also well suited to qualify new production processes.

The method of the present invention has been experimentally tested using a number of wafers each with a different metal layer thickness. The metal that was used was an aluminum copper layer in which the copper made up one half of one percent of the metal layer (0.5% copper). The thickness of metal layer on the five semiconductor wafers was (1) two thousand Ångstroms (2,000 Å), (2) four thousand five hundred Ångstroms (4,500 Å), (3) eight thousand five hundred Ångstroms (8,500 Å), (4) twenty thousand Ångstroms (20,500 Å), and (5) forty thousand Ångstroms (40,500 Å).

With the exception of the metal layer with a two thousand Ångstroms (2,000 Å) thickness, a metal etch process was applied to partially etch the metal layers to approximately the same thickness. The metal layer with a two thousand Ångstroms (2,000 Å) thickness was not etched because it was used as a control wafer.

Figure 4:
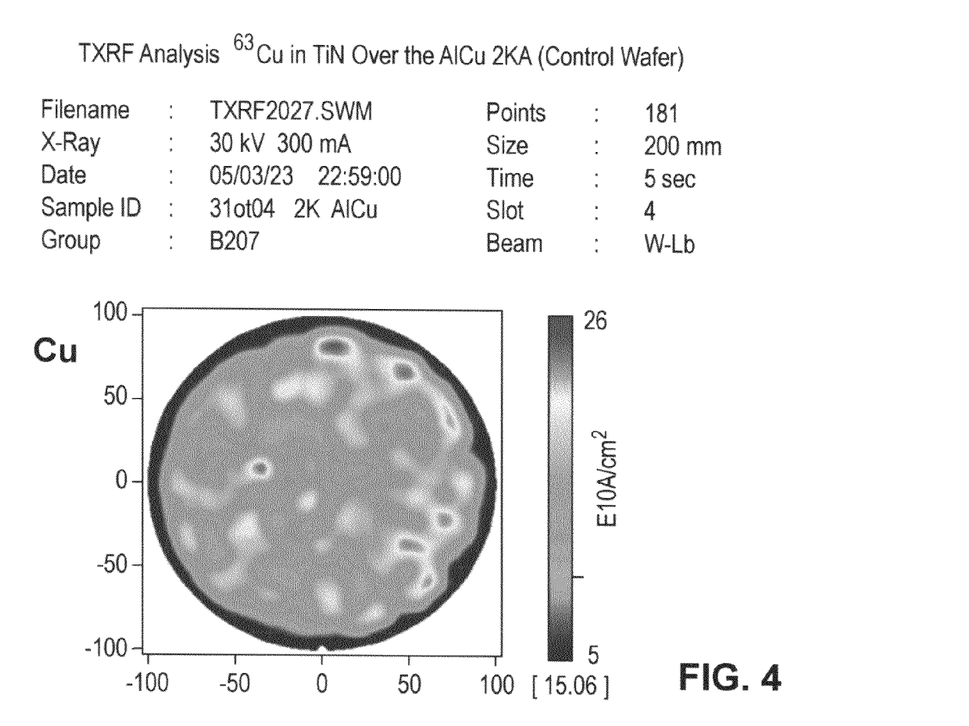
FIG. 4 illustrates a diagram showing a result of a total X-ray reflection fluorescence (TXRF) analysis of copper in a wafer that has an unetched metal layer of aluminum copper that is two thousand Ångstroms (2,000 Å) thick.

The five wafers were then scanned in a surface profiling (SP) total X-ray reflection fluorescence (TXRF) tool. The results of the scans are shown in FIGS. 4 through 8 below. FIG. 4 illustrates a diagram 400 showing a result of the scan of the control wafer having a metal layer that is two thousand Ångstroms (2,000 Å) thick. There is no chlorine in the scan because the control wafer was not etched and was not subjected to chlorine. The concentration of copper atoms is measured in units of $10^{10}$ atoms per square centimeter.

Figure 5:
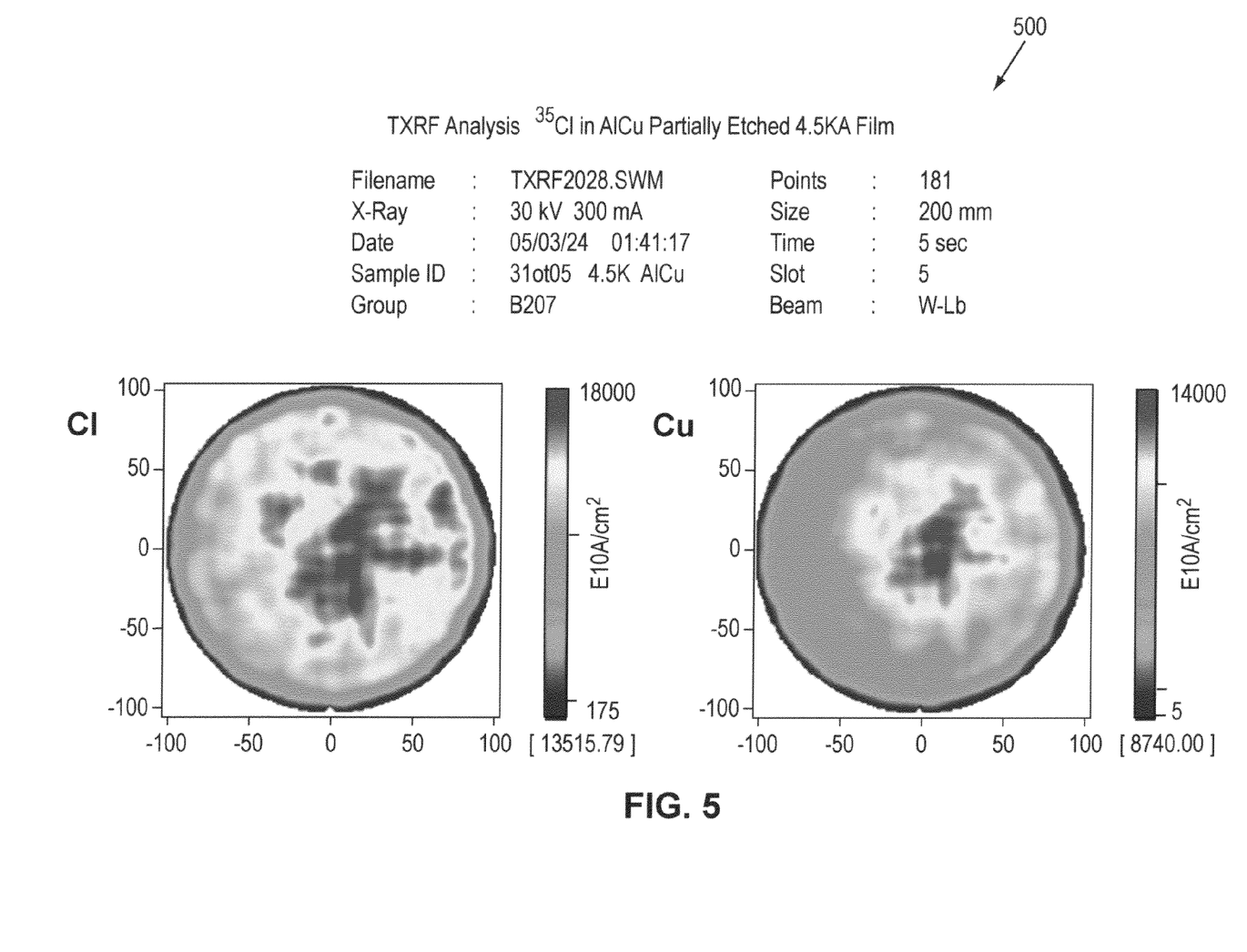
FIG. 5 illustrates a diagram showing a result of a total X-ray reflection fluorescence (TXRF) analysis of chlorine and copper in a wafer that has an etched metal layer of aluminum copper that is four thousand five hundred Ångstroms (4,500 Å) thick.

FIG. 5 illustrates a diagram 500 showing a result of the scan of the control wafer having a metal layer that is four thousand five hundred Ångstroms (4,500 Å) thick. The scan provides a chlorine concentration map showing both quantitative information and spatial information for the chlorine on the surface of the wafer. The scan also provides a copper concentration map showing the both quantitative information and spatial information for the copper on the surface of the wafer. The concentration of copper atoms and the concentration of chlorine atoms are both measured in units of $10^{10}$ atoms per square centimeter.

Figure 6:
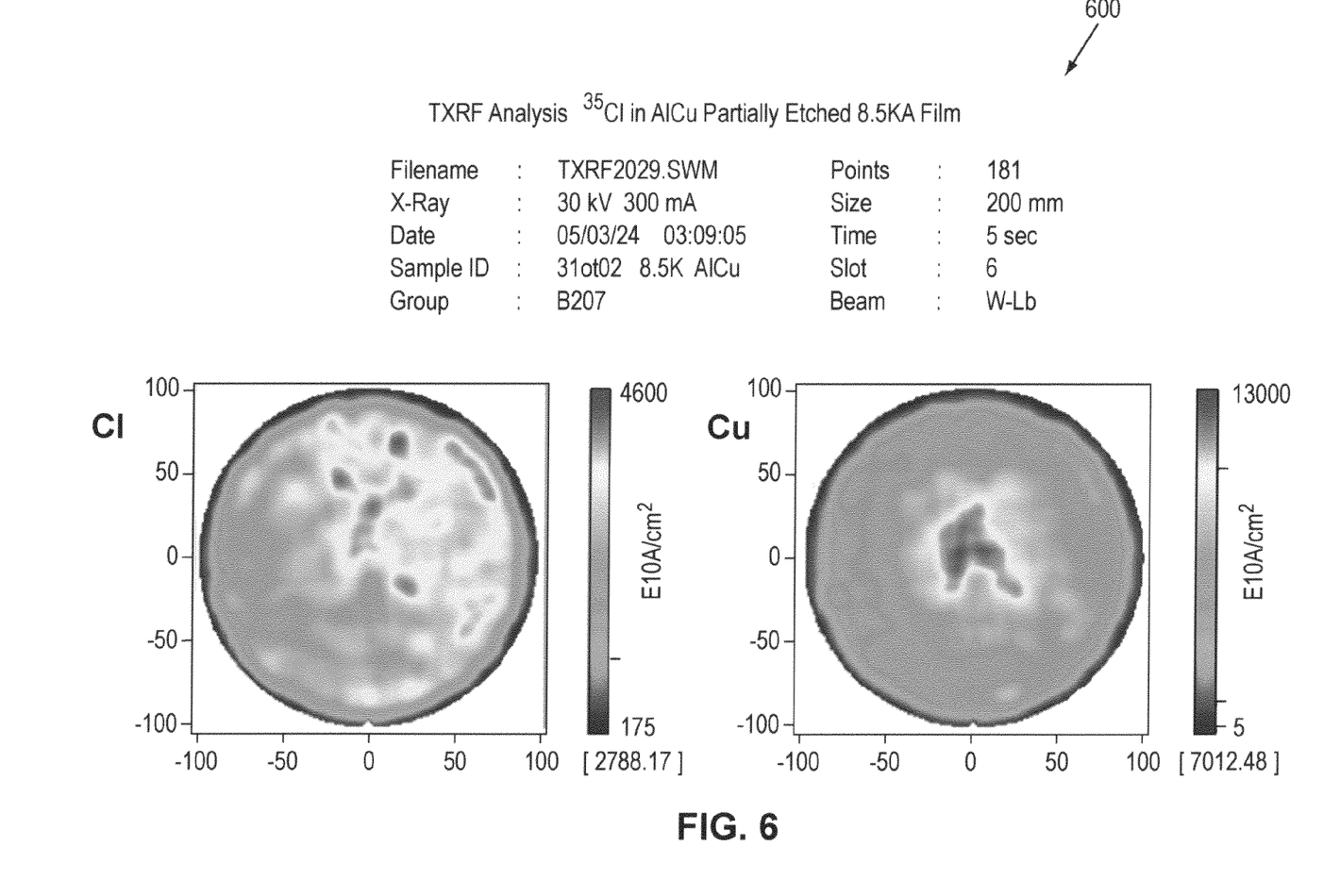
FIG. 6 illustrates a diagram showing a result of a total X-ray reflection fluorescence (TXRF) analysis of chlorine and copper in a wafer that has an etched metal layer of aluminum copper that is eight thousand five hundred Ångstroms (8,500 Å) thick.

FIG. 6 illustrates a diagram 600 showing a result of the scan of the control wafer having a metal layer that is eight thousand five hundred Ångstroms (8,500 Å) thick. The scan provides a chlorine concentration map showing both quantitative information and spatial information for the chlorine on the surface of the wafer. The scan also provides a copper concentration map showing the both quantitative information and spatial information for the copper on the surface of the wafer. The concentration of copper atoms and the concentration of chlorine atoms are both measured in units of $10^{10}$ atoms per square centimeter.

Figure 7:
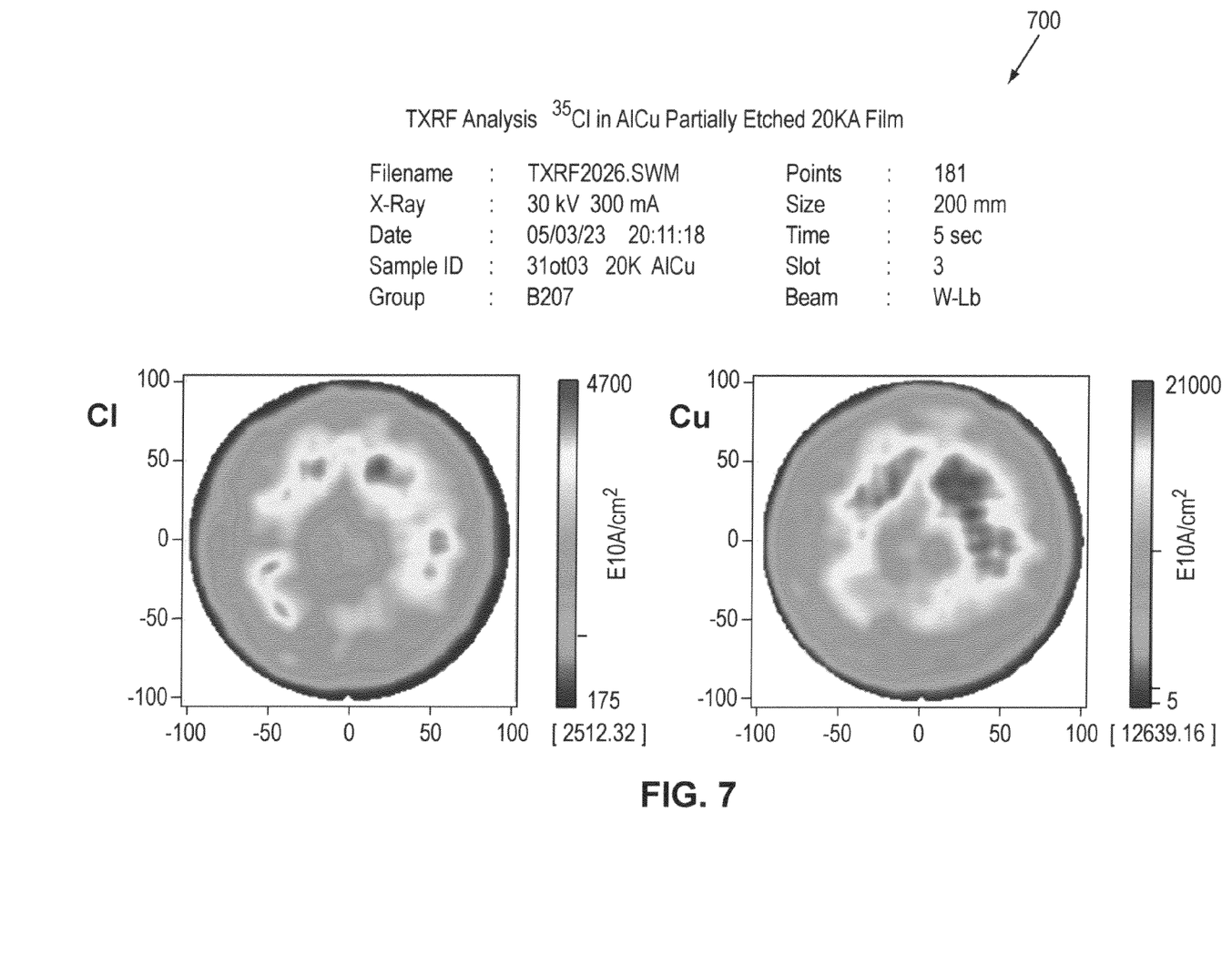
FIG. 7 illustrates a diagram showing a result of a total X-ray reflection fluorescence (TXRF) analysis of chlorine and copper in a wafer that has an etched metal layer of aluminum copper that is twenty thousand Ångstroms (20,000 Å) thick.

FIG. 7 illustrates a diagram 700 showing a result of the scan of the control wafer having a metal layer that is twenty thousand Ångstroms (20,000 Å) thick. The scan provides a chlorine concentration map showing both quantitative information and spatial information for the chlorine on the surface of the wafer. The scan also provides a copper concentration map showing the both quantitative information and spatial information for the copper on the surface of the wafer. The concentration of copper atoms and the concentration of chlorine atoms are both measured in units of $10^{10}$ atoms per square centimeter.

Figure 8:
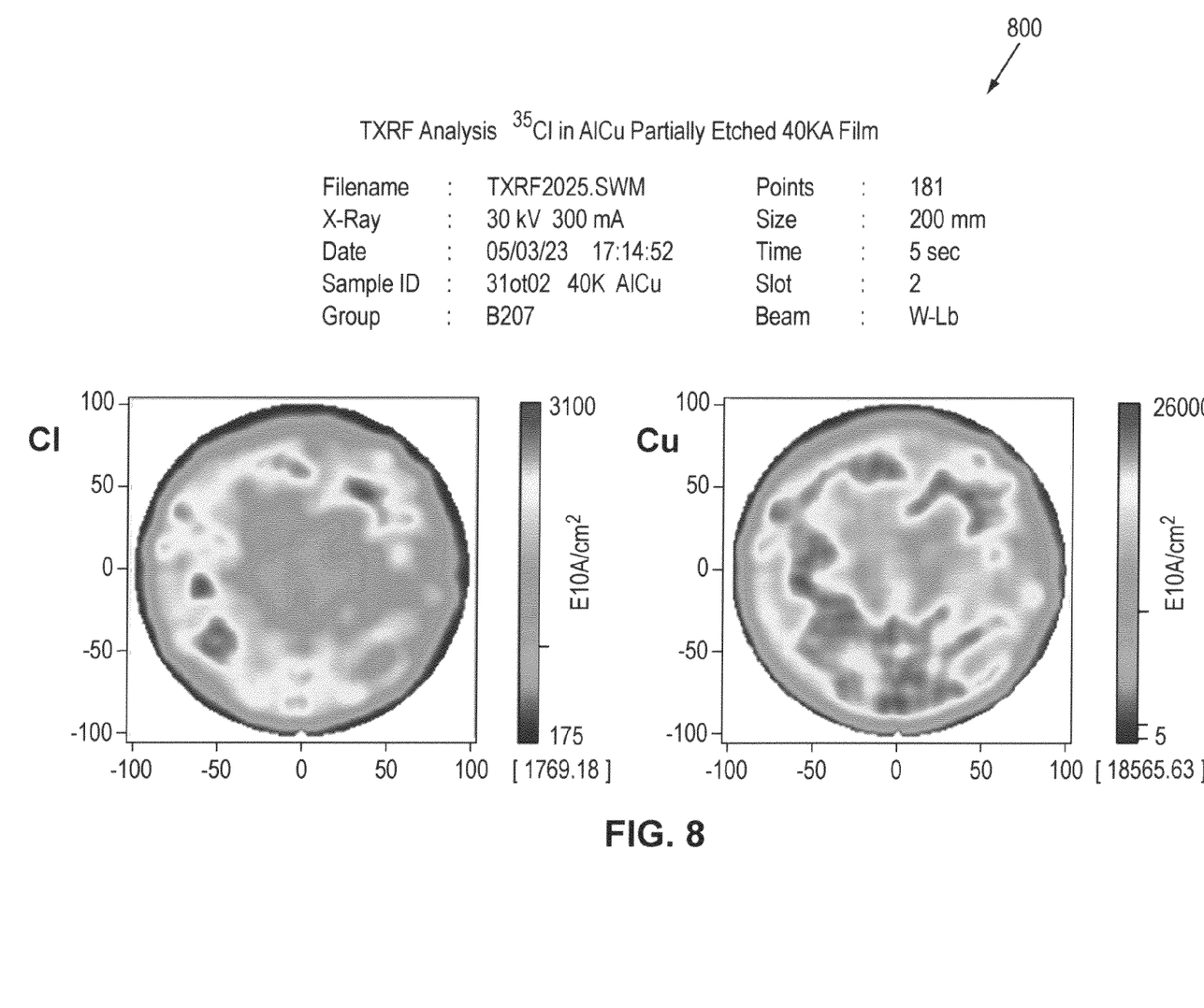
FIG. 8 illustrates a diagram showing a result of a total X-ray reflection fluorescence (TXRF) analysis of chlorine and copper in a wafer that has an etched metal layer of aluminum copper that is forty thousand Ångstroms (40,000 Å) thick.

FIG. 8 illustrates a diagram 800 showing a result of the scan of the control wafer having a metal layer that is forty thousand Ångstroms (40,000 Å) thick. The scan provides a chlorine concentration map showing both quantitative information and spatial information for the chlorine on the surface of the wafer. The scan also provides a copper concentration map showing the both quantitative information and spatial information for the copper on the surface of the wafer. The concentration of copper atoms and the concentration of chlorine atoms are both measured in units of $10^{10}$ atoms per square centimeter.

An additional experimental test was made to confirm the validity of the method of the present invention for the five test wafers. A secondary ion mass spectrometry (SIMS) depth profile analysis of the chlorine in the five test wafers was performed. The SIMS depth profile analysis was performed using five hundred electron volts (500 eV) of primary sputtering energy for cesium (Cs) atoms.

Figure 9:
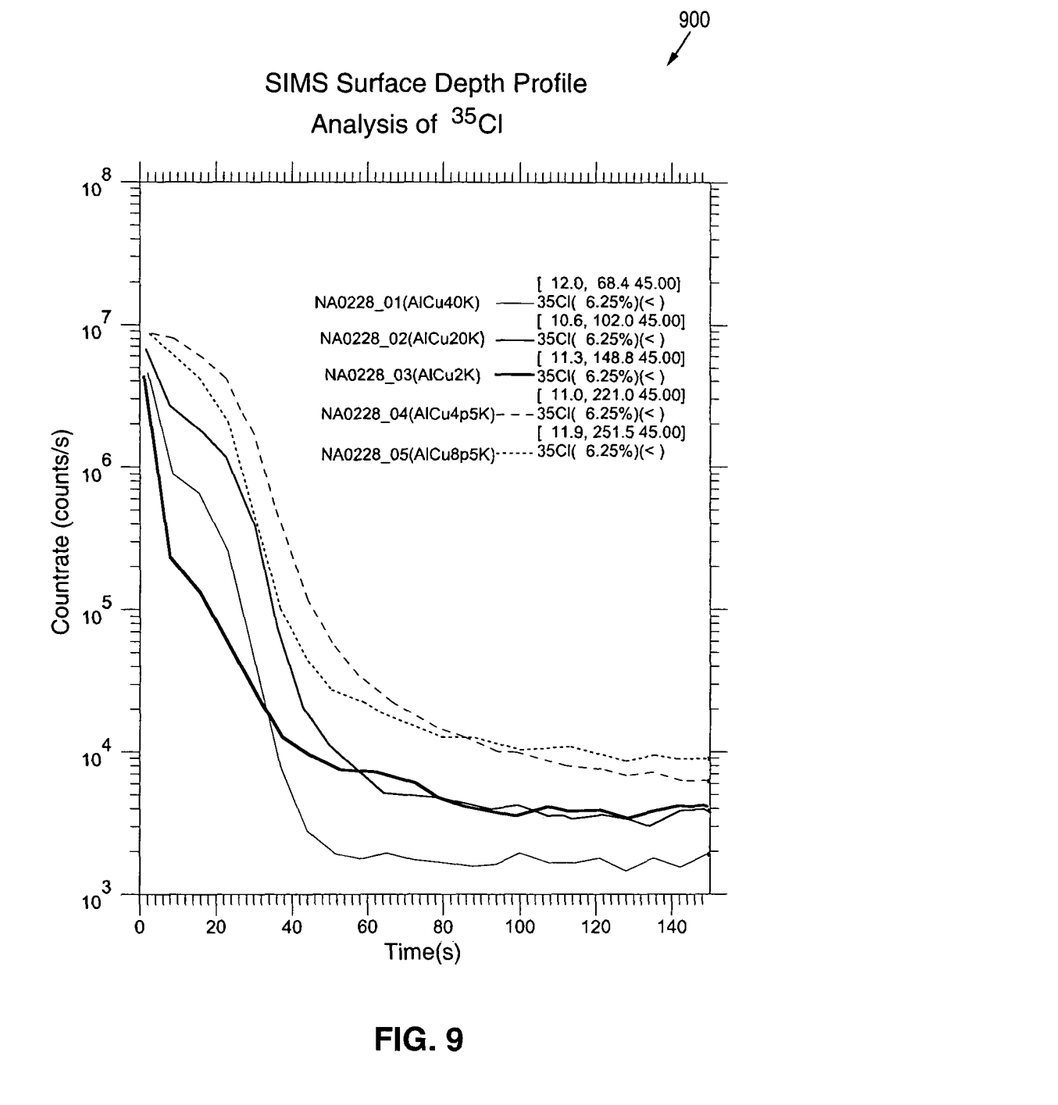
FIG. 9 illustrates a graph of a count rate versus time showing a result of a secondary ion mass spectrometry (SIMS) surface depth profile analysis of chlorine in the wafers described in FIGS. 4 through 8.

FIG. 9 illustrates a graph 900 showing the results of the SIMS depth profile analysis of chlorine for the five wafers. The vertical scale of graph 900 shows the count rate (in counts/second) and the horizontal scale of graph 900 shows time (in seconds). The time represents the depth within the wafer. The zero time represents the surface of the wafer. The concentration of the chlorine is highest at the surface and declines the deeper one goes into the surface of the wafer. This confirms that the chlorine contamination is a primarily a surface effect. The results of SIMS surface depth profile analysis of chlorine in the five wafers confirms the validity of the method of the present invention.

Figure 10:
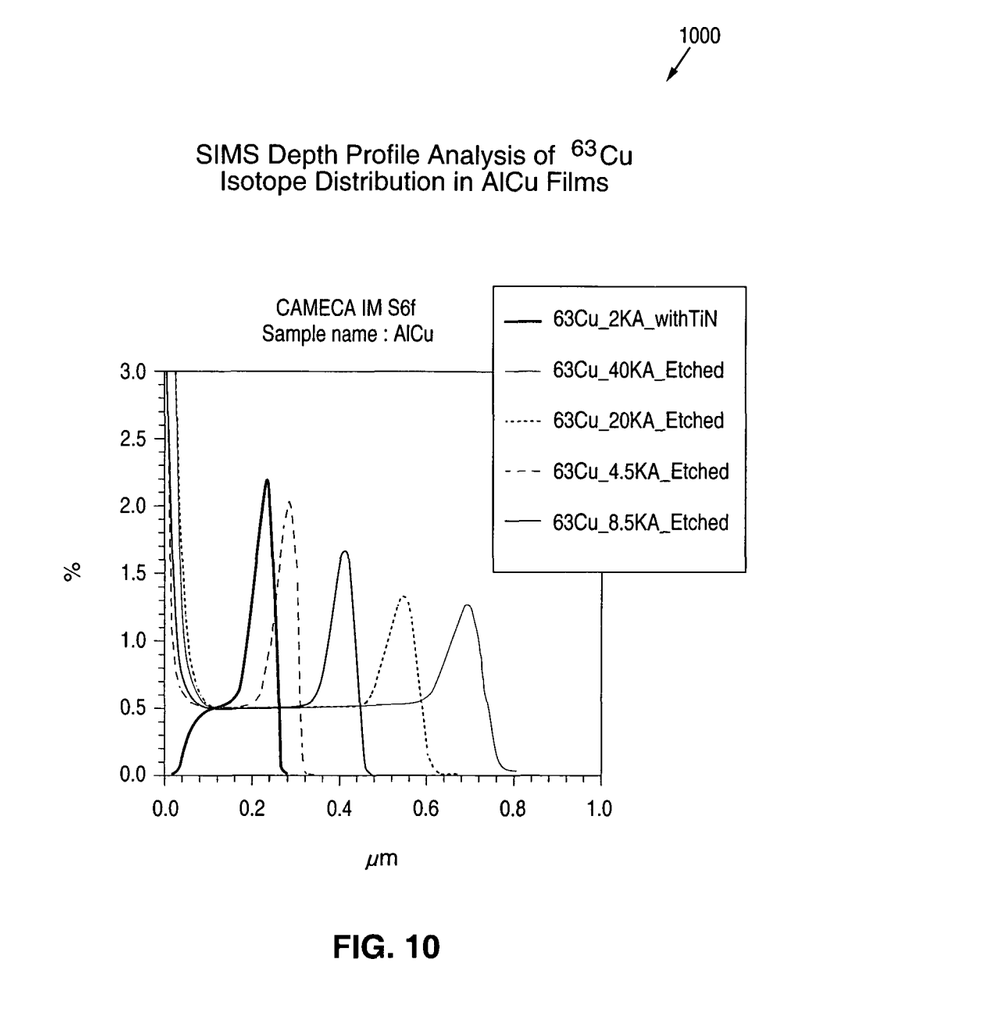
FIG. 10 illustrates a graph of a count rate versus time showing a result of a secondary ion mass spectrometry (SIMS) depth profile analysis of a copper isotope distribution in the wafers described in FIGS. 4 through 8.

A secondary ion mass spectrometry (SIMS) depth profile analysis of a copper isotope ($^{63}$Cu) in the five test wafers was also performed. FIG. 10 illustrates a graph 1000 showing a result of a secondary ion mass spectrometry (SIMS) depth profile analysis of the copper isotope distribution in the wafers described in five test wafers. The vertical scale of graph 1000 measures a percentage (%) of copper isotope detected. The horizontal scale of graph 1000 measures a depth of the wafer in microns.

There is an initial spike in the count of copper atoms near the surface of each wafer. This is a normal occurrence. Then the concentration falls off to a lower level as one proceeds deeper into the wafer. A peak that represents a higher concentration of copper atoms is encountered at a deeper depth in the wafer. The SIMS results in graph 1000 correspond to the surface profiling (SP) total X-ray reflection fluorescence (TXRF) data concerning the copper distribution from each of the five wafers. The SIMS results in graph 1000 also correspond to the levels of copper precipitation variation according to aluminum (Al) grain size (the interface copper (Cu) peak). The results of SIMS depth profile analysis of copper in the five wafers also confirms the validity of the method of the present invention.

The method of the invention provides significant advantages over the prior art methods. The method of the invention is capable of efficiently monitoring chloride content and concentration in semiconductor wafers. The method of the invention also provides quantitative information with much greater precision that the prior art. In addition, the method of the invention may be performed very quickly compared to the prior art methods. Lastly, the method of the invention enables one to determine a value of chlorine concentration for a metal etch process that will not create metal chloride corrosion.

The foregoing description has outlined in detail the features and technical advantages of the present invention so that persons who are skilled in the art may understand the advantages of the invention. Persons who are skilled in the art should appreciate that they may readily use the conception and the specific embodiment of the invention that is disclosed as a basis for modifying or designing other structures for carrying out the same purposes of the present invention. Persons who are skilled in the art should also realize that such equivalent constructions do not depart from the spirit and scope of the invention in its broadest form.

Although the present invention has been described with an exemplary embodiment, various changes and modifications may be suggested to one skilled in the art. It is intended that the present invention encompass such changes and modifications as fall within the scope of the appended claims.

What is claimed is:

1. A method comprising the steps of:
    placing a semiconductor wafer in a total X-ray reflection fluorescence tool;
    scanning said semiconductor wafer using total X-ray reflection fluorescence;
    determining a chlorine content and a copper content of said semiconductor wafer through surface profiling of said semiconductor wafer, wherein said surface profiling determines said chlorine content and said copper content through said total X-ray reflection fluorescence; and
    using said determination of said chlorine content of said semiconductor wafer and chlorine contents and copper contents for a plurality of semiconductor wafers previously exposed to a metal etch process to select a value of chlorine concentration for said metal etch process to etch said semiconductor wafer that will not create metal chloride corrosion on the semiconductor wafer;
    wherein said plurality of semiconductor wafers were previously exposed to said metal etch process with a plurality of chlorine concentrations; and
    wherein said total X-ray reflection fluorescence creates a copper concentration map showing quantitative and spatial information for copper on a surface of said semiconductor wafer.

2. The method as set forth in claim 1 further comprising the step of:
    generating a chlorine concentration map of said semiconductor wafer from said chlorine content derived by said total X-ray reflection fluorescence.

3. The method as set forth in claim 2 further comprising the step of:
    obtaining quantitative information about said chlorine content of said semiconductor wafer from said chlorine concentration map.

4. The method as set forth in claim 2 further comprising the step of:

obtaining quantitative information about a chlorine concentration of said semiconductor wafer from said chlorine concentration map.

5. The method as set forth in claim 2 further comprising the step of:
obtaining spatial information about said chlorine content of said semiconductor wafer from said chlorine concentration map.

6. The method as set forth in claim 2 further comprising the step of:
obtaining spatial information about a chlorine concentration of said semiconductor wafer from said chlorine concentration map.

7. The method as set forth in claim 2 further comprising the steps of:
using information from said chlorine concentration map to identify a threshold value of chlorine concentration for said metal etch process below which said metal etch process will not create said metal chloride corrosion on subsequent semiconductor wafer; and
maintaining a level of chlorine concentration in said metal etch process below said threshold value of chlorine concentration during etching of said subsequent semiconductor wafer using said metal etch process.

8. A method comprising the steps of:
placing a semiconductor wafer that has been subjected to a metal etch process in a total X-ray reflection fluorescence tool;
scanning said semiconductor wafer using total X-ray reflection fluorescence;
determining a chlorine content and a copper concentration at multiple points on the semiconductor wafer through surface profiling of said semiconductor wafer, wherein said surface profiling determines said chlorine content through said total X-ray reflection fluorescence and a copper concentration map created from said X-ray reflection fluorescence showing quantitative and spatial information for copper on a surface of said semiconductor wafer; and
using said determination of chlorine content to select a value of chlorine concentration for said metal etch process that will not create metal chloride corrosion on a subsequent semiconductor wafer subjected to said metal etch process.

9. The method as set forth in claim 8 further comprising the steps of:
generating a chlorine concentration map of said semiconductor wafer using said quantitative and spatial information derived by said total X-ray reflection fluorescence; and
using said chlorine concentration map to identify metal chloride on said semiconductor wafer.

10. The method as set forth in claim 9 further comprising the steps of:
obtaining quantitative information about said chlorine content of said semiconductor wafer from said chlorine concentration map; and
using said quantitative information about said chlorine content of said semiconductor wafer to identify at least one amount of metal chloride on said semiconductor wafer.

11. The method as set forth in claim 9 further comprising the steps of:
obtaining quantitative information about a chlorine concentration of said semiconductor wafer from said chlorine concentration map; and
using said quantitative information about said chlorine concentration of said semiconductor wafer to identify at least one amount of metal chloride on said semiconductor wafer.

12. The method as set forth in claim 9 further comprising the steps of:
obtaining spatial information about said chlorine content of said semiconductor wafer from said chlorine concentration map; and
using said spatial information about said chlorine content of said semiconductor wafer to identify at least one location of metal chloride on said semiconductor wafer.

13. The method as set forth in claim 9 further comprising the steps of:
obtaining spatial information about a chlorine concentration of said semiconductor wafer from said chlorine concentration map; and
using said spatial information about said chlorine concentration of said semiconductor wafer to identify at least one location of metal chloride on said semiconductor wafer.

14. The method as set forth in claim 9 further comprising the steps of:
using information from said chlorine concentration map to identify a threshold value of chlorine concentration for said metal etch process below which said metal etch process will not create said metal chloride corrosion on said subsequent semiconductor wafer; and
maintaining a level of chlorine concentration in said metal etch process below said threshold value of chlorine concentration during etching of said subsequent semiconductor wafer using said metal etch process.

15. A method comprising the steps of:
subjecting a semiconductor wafer to a metal etch process that exposes said semiconductor wafer to chlorine;
placing said semiconductor wafer in a total X-ray reflection fluorescence tool;
scanning said semiconductor wafer using total X-ray reflection fluorescence;
determining a chlorine content and a copper concentration map through surface profiling of said semiconductor wafer, wherein said surface profiling determines said chlorine content through said total X-ray reflection fluorescence, and wherein said copper concentration map is created by said total X-ray reflection fluorescence and shows quantitative and spatial information for copper on a surface of said semiconductor wafer; and
using said determination of chlorine content to select a value of chlorine concentration for said metal etch process that will not create metal chloride corrosion on a subsequent semiconductor wafer subjected to said metal etch process.

16. The method as set forth in claim 15 further comprising the steps of:
generating a chlorine concentration map of said semiconductor wafer using said chlorine content derived by said total X-ray reflection fluorescence; and
using said chlorine concentration map to identify an amount of metal chloride on said semiconductor wafer.

17. The method as set forth in claim 16 wherein said selected value of chlorine concentration is determined from information from said chlorine concentration map.

18. The method as set forth in claim 16 further comprising the steps of:
using information from said chlorine concentration map to identify a threshold value of chlorine concentration for said metal etch process below which said metal etch process will not create said metal chloride corrosion on said subsequent semiconductor wafer; and maintaining a level of chlorine concentration in said metal etch process below said threshold value of chlorine concentration during etching of said subsequent semiconductor wafer using said metal etch process.

19. The method as set forth in claim 16 further comprising the steps of:

obtaining quantitative information about said chlorine content of said semiconductor wafer from said chlorine concentration map; and using said quantitative information about said chlorine content of said semiconductor wafer to identify at least one amount of metal chloride on said semiconductor wafer.

20. The method as set forth in claim 16 further comprising the steps of:

obtaining quantitative information about a chlorine concentration of said semiconductor wafer from said chlorine concentration map; and using said quantitative information about said chlorine concentration of said semiconductor wafer to identify at least one amount of metal chloride on said semiconductor wafer.

* * * * *